(12) United States Patent
Weibrecht et al.

(10) Patent No.: US 7,835,556 B2
(45) Date of Patent: Nov. 16, 2010

(54) SYSTEM AND METHOD FOR DIAGNOSING BREAST CANCER

(75) Inventors: Martin Weibrecht, Aachen (DE); Joerg Bredno, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 1037 days.

(21) Appl. No.: 11/568,993

(22) PCT Filed: Apr. 29, 2005

(86) PCT No.: PCT/IB2005/051409
§ 371 (c)(1),
(2), (4) Date: Nov. 13, 2006

(87) PCT Pub. No.: WO2005/110230
PCT Pub. Date: Nov. 24, 2005

(65) Prior Publication Data
US 2007/0225600 A1 Sep. 27, 2007

(30) Foreign Application Priority Data
May 14, 2004 (EP) .................................. 04102114

(51) Int. Cl.
*A61B 5/05* (2006.01)
*G06K 9/00* (2006.01)
(52) U.S. Cl. ....................................... 382/128; 600/429
(58) Field of Classification Search ......... 382/128–132; 600/427, 429
See application file for complete search history.

(56) References Cited
U.S. PATENT DOCUMENTS
5,209,232 A * 5/1993 Levene ........................ 600/427

(Continued)

FOREIGN PATENT DOCUMENTS
EP 1047018 A1 10/2000

(Continued)

OTHER PUBLICATIONS
International Search Report of Intl. Application No. PCT/IB2005/051409 Contained in Intl. Publication No. WO2005110230, Aug. 2, 2005.

(Continued)

*Primary Examiner*—Vu Le
*Assistant Examiner*—Amara Abdi

(57) ABSTRACT

The invention relates to a system and a method for the investigation of a body volume (3), particularly for the diagnosis of breast cancer According to the method, a sequence of X-ray projections (P, P') from different directions is produced by a rotatable X-ray source (1) and a stationary digital X-ray detector (5). From these projections (P, P'), a set of sectional images (a, b, c, d) is calculated by tomosynthesis. A physician may indicate a suspicious structure on a reference image (R) that is derived from one of the projections (P, P') or sectional images (a, b, c, d) and displayed on a monitor (6). The computer (7) may then locate the structure on all sectional images (a, b, c, d) and calculate the similarity of a corresponding image feature. The sectional 10 image at which the similarity is strongest then indicates the depth (zo) at which the structure (4) is positioned in the body volume (3). Based on this information, a biopsy device (9) with a needle (10) can be advanced into the body volume (3) until it reaches the suspicious structure (4).

14 Claims, 1 Drawing Sheet

U.S. PATENT DOCUMENTS

Figure 1:
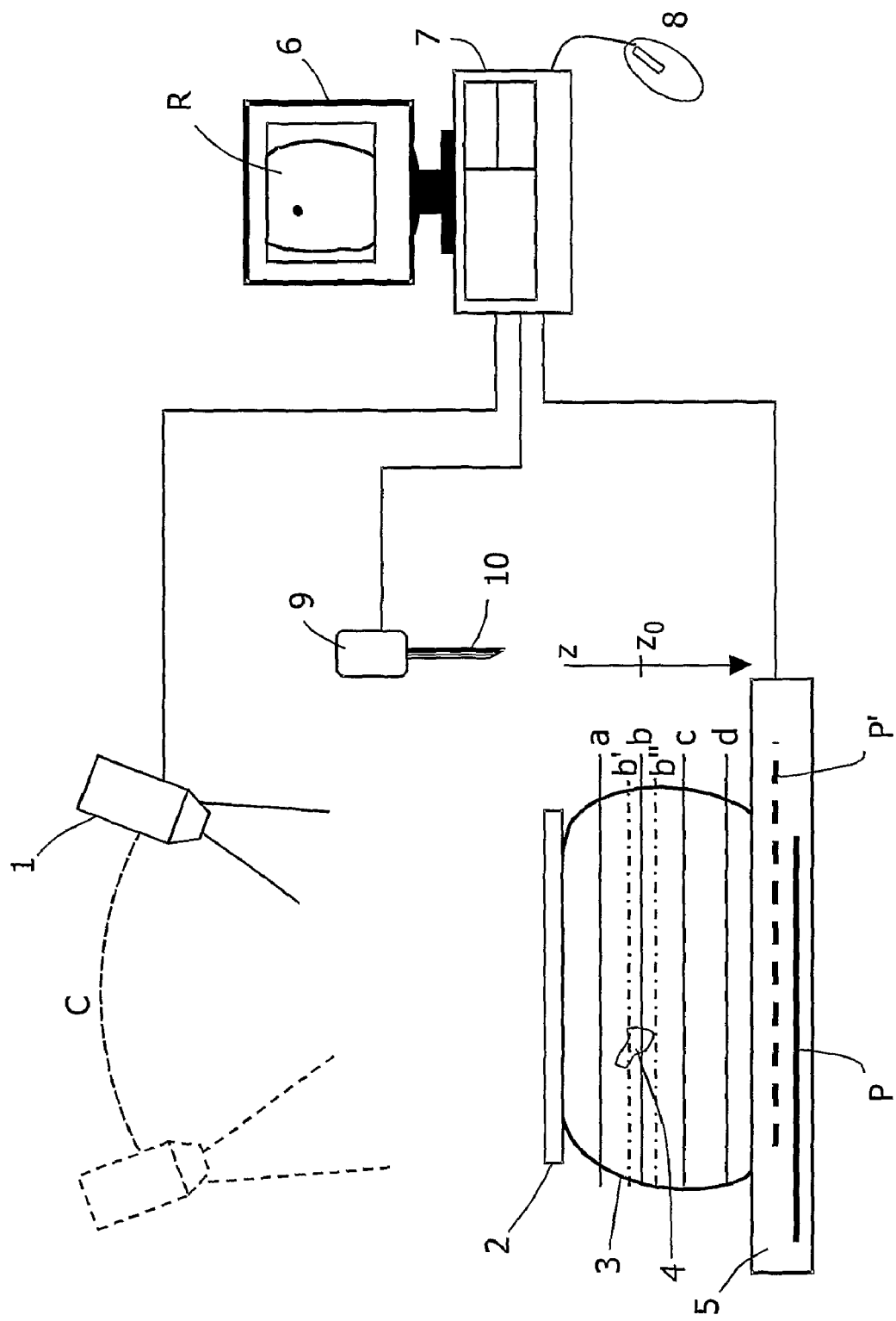

| | | | |
|---|---|---|---|
| 5,594,769 A * | 1/1997 | Pellegrino et al. | 378/37 |
| 5,872,828 A | 2/1999 | Niklason et al. | |
| 5,970,164 A * | 10/1999 | Bamberger et al. | 382/128 |
| 6,375,352 B1 | 4/2002 | Hewes et al. | |
| 6,611,575 B1 * | 8/2003 | Alyassin et al. | 378/37 |
| 2002/0172414 A1 | 11/2002 | Muller et al. | |
| 2003/0109779 A1 * | 6/2003 | Ohishi et al. | 600/407 |
| 2004/0008809 A1 | 1/2004 | Webber | |
| 2005/0113681 A1 * | 5/2005 | DeFreitas et al. | 600/426 |

FOREIGN PATENT DOCUMENTS

| | | |
|---|---|---|
| EP | 1314976 A2 | 5/2003 |
| FR | 2751109 A1 | 1/1998 |

OTHER PUBLICATIONS

Written Opinion of the International Searching Authority for Intl. Application No. PCT/IB2005/051409, Aug. 2, 2005.

Allyassin et al: "3D Visualization of X-Ray Tomosynthesis Digital Mammography Data: Preference Study"; GE Technical Report, Aug. 2002, Report No. 2002GRC207.

* cited by examiner

SYSTEM AND METHOD FOR DIAGNOSING BREAST CANCER

The invention relates to a system and a method for the investigation of a body volume, particularly for diagnosing breast cancer.

In breast cancer diagnostics, suspicious tissues are identified on X-ray mammographs where the compression of the breast required for diagnostic image quality is a severe strain for patients. Reliable tissue characterization often requires a biopsy. To determine the depth in the compressed breast where the biopsy needle must extract suspicious tissue, usually a stereotactic framework is applied (cf. U.S. Pat. No. 5,594,769): Two images are acquired and a trained user has to identify suspicious tissue in two views and mark theses spots mechanically on film or with mouse clicks so that the depth of the biopsy can be computed. The variability of this computation is usually high because two precise localizations are required for a robust depth estimation.

Based on this situation it was an object of the present invention to provide means for a more reliable and faster diagnosis of breast cancer, especially in connection with the extraction of a biopsy.

This object is achieved by a system according to claim 1 and a method according to claim 9. Preferred embodiments are subject of the dependent claims.

The system according to the present invention may be used for the investigation of a body volume, particularly for diagnosing breast cancer. It comprises the following components:

An X-ray device for generating projections of the body volume from different directions.

A data processing unit that is coupled to said X-ray device and adapted to reconstruct from said projections sectional images of the body volume at different depths, wherein the depth of a section through the body volume is measured with reference to a predetermined axis, preferably an axis vertical to the plane of the projections of the X-ray device.

An indication device for interactively indicating a structure of interest in a so-called "reference image" which is one of said projections and/or an image derived from said projections or the sectional images. The indication device may for example be a mouse, a stick or a set of keys with which a cursor can be moved across a screen, a touch screen, or any other suitable pointing or input device.

Moreover, the data processing unit of the system is adapted to estimate the depth of said structure in the body volume with the help of said sectional images. This estimation may be executed in different ways, some of which are described with reference to preferred embodiments of the invention.

The described system may especially be used in the diagnosis of breast cancer, where often a biopsy must be made for a reliable diagnosis of suspicious tissue. In order to perform such a biopsy, it is necessary to know as exactly as possible the position of the suspicious structure within the body volume. This information is gained with said system in a fast and rather simple way by generating X-ray projections, calculating sectional images from these projections, and determination of the required depth, i.e. of the spatial position of the structure in said body volume, with the help of these sectional images.

One preferred way to estimate the depth of the structure of interest comprises the following steps:

a) Determination of a reference feature vector with at least one image feature of said indicated structure of interest on the reference image.

Image features may for example include a set of pixel values taken from the neighborhood of the interesting structure in the (high-pass filtered) image, the contrast of the structure with respect to its surroundings, the width or the area of the structure (after determination of its boundaries), and/or measures describing the texture of the structure. Such features may be determined (and quantified) with known methods of image processing.

b) Determination of said feature vector in all sectional images at the location that corresponds to the location of the structure of interest on the reference image. These corresponding locations may easily be determined due to the known geometrical relationships between the different projections and sectional images. Moreover, the similarity between the reference feature vector and the feature vectors for each sectional image is quantified. For this step, a suitable measure for the similarity of the feature vectors is required, wherein said similarity of the feature vectors shall reflect the probability with which the structure of interest is present in the sectional image under investigation.

c) The determination of the depth at which said similarity of the feature vectors has an extreme value, particularly a maximum. This depth will then be taken as the desired estimated depth of the structure of interest in the body volume.

According to the embodiment described above, a suspicious structure may for example be identified by a physician on a projection image of a breast, and the data processing unit then automatically scans all sectional images to find the corresponding location of said structure and to determine on which sectional image the structure is represented most similarly to its representation on the reference image. The depth of the corresponding sectional image may then be taken as the value of the required depth of the structure of interest. The depth may of course also be calculated as an interpolation of the depths of several sectional images, for example as a weighted average of depths of two neighboring sectional images. Moreover, it should be noted that the sequence of steps a)-c) may be rearranged, that some of these steps may be repeated and/or that further steps may be added.

The X-ray device may particularly comprise an X-ray source that can be moved along a given trajectory, wherein the trajectory is preferably a straight line or a (circular) arc. Movement of the X-ray detector along a circular arc is particularly simple to realize because the X-ray source may then simply be fixed to the end of a pivoted arm, guaranteeing at the same time that the X-ray source is always directed to the centre of rotation. Moreover, the X-ray detector is a digital X-ray detector in this case. Such an X-ray detector may remain stationary while the X-ray source moves and creates projections onto the detector from different directions.

In a further development of the system, which may particularly be combined with the aforementioned embodiment, the data processing unit is adapted to generate tomosynthetic images of the body volume. In tomosynthesis, projections of a body from different directions are combined after scaling and/or shifting in order to reconstruct a sectional image at a certain depth of the body volume. X-ray devices for tomosynthesis in the diagnosis of breast cancer are for example described in the U.S. Pat. Nos. 6,611,575 B1 and 5,872,828, which documents are incorporated into the present application by reference.

The system further comprises a display device like a monitor for displaying said projections and/or said sectional images of the body volume. A physician may then inspect these images on the display in order to make his diagnosis.

The system may further comprise an input device for inputting a continuous value, wherein the value controls the choice of a sectional image that shall be processed (for example displayed on a display unit mentioned above). The input device may for instance be a mouse wheel that can be rotated by a user to produce an angle of rotation as a continuous signal value. The value produced by the input device can optionally be mapped to a depth in the body volume, and the sectional image to be processed may then be chosen as the one that is located next to said depth.

According to further development of the system it comprises a biopsy device with a needle for extracting a sample of the structure of interest, said device being controlled by the data processing unit. As the data processing unit is able to calculate the depth of a suspicious structure, this information may particularly be used to control precisely the advancement of a needle in a biopsy that is executed in order to gain a reliable diagnosis.

Moreover, the system may be adapted to reconstruct additional sectional images of the body volume for a fine-tuning of the depth estimation. This reconstruction may for example be done after a coarse value for the depth has been estimated with the help of the available sectional images, wherein the additional images are calculated in depths near said coarse value.

The invention further concerns a method for the investigation of a body volume, particularly for diagnosing breast cancer, the method comprising the following steps:
  a) Generating X-ray projections of the body volume from different directions.
  b) Reconstructing sectional images of the body volume at different depths based on said projections.
  c) Displaying at least one of the projections and/or a derivative of the sectional images as a reference image in order to allow an interactive indication of a structure of interest.
  d) Estimating the depth of said structure in the body volume with the help of the sectional images.

The method comprises in general form the steps that can be executed with a system of the kind described above. Therefore, reference is made to the preceding description for more information on the details, advantages and improvements of that method.

The estimation of the depth of the structure of interest may particularly comprise the following steps:
  a) Determination of a reference feature vector with at least one image feature of said indicated structure of interest on the reference image.
  b) Determination of said feature vector at the corresponding locations in all sectional images and quantification of its similarity to the reference feature vector.
  c) Determination of the depth at which said similarity of the feature vectors has an extreme value.

According to a further development of the method, an instrument is advanced into the body volume to the estimated depth of said structure of interest. The instrument may particularly be a needle for taking a biopsy of said structure.

These and other aspects of the invention will be apparent from and elucidated with reference to the embodiment(s) described hereinafter.

In the following the invention is described by way of example with the help of the accompanying drawing which schematically represents a system for diagnosing breast cancer according to be present invention.

The system in the Figure comprises an X-ray imaging device with an X-ray source 1 and a digital flat dynamic X-ray detector 5. The system is used for diagnosing breast cancer, wherein a breast 3 is located as usual on the X-ray detector 5 and compressed by a flat plate 2 that is transparent to X-rays. When the breast 3 is irradiated with a beam of X-rays from the X-ray source 1, a projection P is produced on the X-ray detector 5.

According to the present invention, the X-ray source 1 can be moved along a predetermined trajectory, for example a circular arc C. During this rotation, the X-ray source 1 is always orientated in such a way that the breast 3 remains in the centre of the irradiation. Moreover, at several (typically about 10 to 50) intermediate positions of the rotation along arc C, the X-ray source emits X-rays and thus produces projections of the breast onto the detector 5 from different directions. In the Figure, only the projections P and P' corresponding to the end positions of the rotation are indicated (wherein a vertical shift between P and P' is only introduced into the drawing for illustrative reasons).

Based on the generated sequence of projections P, ... P', a data processing unit 7 (workstation) that is coupled to the X-ray device can calculate sectional images a, b, c, d through the breast 3 parallel to the plane of the detector 5 at different depths z (measured for example perpendicular to the plate 2). The calculation may be done according to the known principles of tomosynthesis. The original projections P, ... P', projective summation images calculated thereof, and/or the calculated sectional images a, b, c, d can be displayed on a monitor 6 that is coupled to the computer 7. The physician may then perform his diagnosis on single projections, projective summation images, or on slice reconstructions.

If the physician has identified a suspicious structure on one of the projections or sectional images, it will often be necessary to take a biopsy in order to gain a reliable diagnosis. The system comprises a biopsy device 9 with a biopsy needle 10 for this purpose. The biopsy needle 10 can be placed above the breast and be advanced into the tissue until a predetermined depth is reached, where a sample of the tissue is extracted.

While the physician can position the needle 10 in the horizontal plane with sufficient accuracy according to the X-ray projections that are available, the depth z to which the needle has to be advanced is more difficult to determine. In the state of the art, stereotactic procedures with X-ray projections from two different directions are used for this purpose. However, these known procedures require a lot of skill and are prone to many influences that deteriorate accuracy. To improve this situation, it is proposed here to use the sectional images a, b, c, d in order to estimate the depth $z_0$ of the suspicious structure. In a preferred embodiment, the proposed method comprises the following steps:

Indication of a suspicious structure 4 in one of the projection images P, ... P' or in a projective summation image calculated thereof that are displayed for this purpose on the monitor 6 as a reference image R. A physician may indicate a suspicious structure on the reference image R for example by clicking on it with a mouse 8 or some similar device.

After indication of the structure, the computer 7 automatically calculates the estimated depth z of this structure 4 in the body volume 3. To this end, the computer 7 first analyses the indicated structure on the reference image R and determines one or more characteristic image features that constitute the components of a "reference" feature vector. An image feature may for instance include texture information, which can be determined by looking at the high-frequency components of the images. Another important example for an image feature is the region that is obtained by segmentation of the structure on the reference image R with the help of appropriate algorithms known from image processing. The area of this region is then simultaneously a suitable quantification of the "magnitude" of the image feature.

The computer 7 then scans all sectional images a, b, c, d and determines the corresponding location of the structure on each sectional image (if it exists). Moreover, the computer 7 determines the feature vector of the structure in each of the sectional images a, b, c, d in the same way as it was determined for the reference image R. The similarity between each of these feature vectors and the reference feature vector of the reference image R is then taken as a measure of how much the structure 4 is actually present in the sectional image under investigation. Suitable similarity measures for this purpose are for example direct chessboard differences, i.e. the sum of all absolute differences of the individual components of the feature vector, or the Mahlanobis distance, which takes into account the variability of the components of the feature vector. The depth $z_0$ of the sectional image on which said similarity is maximal is then assumed to be the required depth of the structure.

In the situation shown in the Figure, the structure 4 will for example show up most sharply (and therefore most similar to its simple projection) on the sectional image b at the depth $z_0$. The depth of the sectional image b, on which the structure of interest is most prominently displayed, therefore indicates the best estimation of the real position of the structure 4 in the body volume 3.

In a further development of this approach, the depth of the structure 4 may be determined as an interpolated value of the depths of two or more neighboring sectional images a, b. Moreover, additional sectional images b', b'', . . . may be reconstructed around a depth $z_0$ from the projections P, . . . P' if the position of the structure 4 is first coarsely predetermined as $z_0$ by the available sectional images and shall then be calculated more precisely.

After the automatic determination of the depth $z_0$ of the structure 4 in the body volume 3, the computer 7 may control the biopsy device 9 such that its needle 10 is advanced into the body volume 3 until the determined depth $z_0$—i.e. the suspicious structure 4—is reached.

When looking at the sectional images a, b, c, d on the monitor 6, the physician may browse through the slices with the help of a suitable control device, for example the wheel of the mouse 8. The physician may then choose a sectional image that already shows the structure of interest 4 rather clearly, thus making it possible to include intuitive vision of the physician into the depth calculation.

In conclusion, the user interaction to determine position and depth of a biopsy is reduced. This results in two independent advantages: The time in which the breast of the patient remains compressed is reduced and the reproducibility and precision of the procedure is increased.

Finally it is pointed out that in the present application the term "comprising" does not exclude other elements or steps, that "a" or "an" does not exclude a plurality, and that a single processor or other unit may fulfill the functions of several means. Moreover, reference signs in the claims shall not be construed as limiting their scope.

The invention claimed is:

1. System for the investigation of a body volume for diagnosing breast cancer, comprising:
an X-ray device for generating projections of the body volume from different directions;
a data processing unit coupled to said X-ray device and adapted to reconstruct, from said projections, sectional images of the body volume at different depths, wherein each sectional image corresponds to a certain depth of the body volume; and
an indication device for interactively indicating a structure of interest in a reference image, the reference image being derived from one selected from the group consisting of (i) said projections, (ii) said sectional images, and (iii) both said projections and said sectional images,
wherein the data processing unit is further adapted to estimate a depth of said indicated structure of interest in the body volume with use of said sectional images and to reconstruct additional sectional images of the body volume around the estimated depth for a fine-tuning of the depth estimation.

2. The system according to claim 1, wherein further the data processing unit is adapted to:
a) determine a reference feature vector of said indicated structure of interest on the reference image;
b) determine a feature vector at corresponding locations of said indicated structure of interest in all sectional images and quantify its similarity to the reference feature vector; and
c) determine the estimated depth of said indicated structure of interest as a depth at which said similarity has an extreme value.

3. The system according to claim 1, wherein the X-ray device comprises (i) an X-ray source that can be moved along a given trajectory, wherein the trajectory includes an arc or a line, and (ii) a digital X-ray detector.

4. The system according to claim 1, wherein the processing unit is adapted to generate tomosynthetic images of the body volume.

5. The system according to claim 1, further comprising:
a display device for displaying one selected from the group consisting of (i) said projections, (ii) said sectional images, and (iii) both said projections and said sectional images of the body volume.

6. The system according to claim 1, further comprising:
an input device for inputting a continuous value which controls a choice of sectional image to be processed.

7. The system according to claim 1, further comprising:
a biopsy device with a needle for extracting a sample of the structure of interest, said biopsy device being controlled by the data processing unit.

8. System for the investigation of a body volume for diagnosing breast cancer, comprising:
an X-ray device for generating projections of the body volume from different directions;
a data processing unit coupled to said X-ray device and adapted to reconstruct sectional images of the body volume at different depths; and
an indication device for interactively indicating a structure of interest in a reference image which is derived from one selected from the group consisting of (i) said projections, (ii) said sectional images, and (iii) both said projections and said sectional images,
wherein the data processing unit is further adapted to estimate a depth of said indicated structure of interest in the body volume with the help of said sectional images, and still further adapted to reconstruct additional sectional images of the body volume for a fine-tuning of the depth estimation.

9. Method for the investigation of a body volume for diagnosing breast cancer, the method comprising:
a) generating X-ray projections of the body volume from different directions;

b) reconstructing sectional images of the body volume at different depths based on said projections, wherein each sectional image corresponds to a certain depth of the body volume;

c) displaying a reference image, the reference image being derived from at least one of one selected from the group consisting of (i) the projections, (ii) the sectional images, and (iii) both the projections and the sectional images in order to allow an interactive indication of a structure of interest in the reference image; and d) estimating a depth of said indicated structure of interest in the body volume with use of the sectional images, wherein reconstructing sectional images further includes reconstructing additional sectional images of the body volume around the estimated depth for a fine-tuning of the depth estimation.

10. The method according to claim 9, wherein the estimation of the depth of the indicated structure of interest includes:

a) determining a reference feature vector of said indicated structure of interest on the reference image;

b) determining a feature vector at corresponding locations of said indicated structure of interest in all sectional images and quantifying its similarity to the reference feature vector; and c) determining the estimated depth of said indicated structure of interest as a depth at which the similarity of the feature vectors has an extreme value.

11. The method according to claim 9, further comprising:

advancing an instrument into the body volume to the estimated depth of said indicated structure of interest.

12. The method according to claim 9, wherein reconstructing sectional images includes generating tomosynthetic images of the body volume.

13. The method according to claim 9, wherein estimating the depth of said structure of interest in the body volume includes scanning all sectional images (i) to find a corresponding location of said structure of interest and (ii) to determine on which sectional image the structure of interest is represented most similarly to its representation on the reference image, wherein the depth of a corresponding sectional image of most similarity is taken as the value of estimated depth of the structure of interest.

14. The system according to claim 1, wherein further the data processing unit is adapted to estimate the depth of said structure of interest in the body volume by scanning all sectional images (i) to find a corresponding location of said structure of interest and (ii) to determine on which sectional image the structure of interest is represented most similarly to its representation on the reference image, wherein the depth of a corresponding sectional image of most similarity is taken as the value of estimated depth of the structure of interest.

* * * * *